(12) United States Patent
Whitten

(10) Patent No.: US 8,853,223 B2
(45) Date of Patent: *Oct. 7, 2014

(54) THERAPEUTIC COMPOSITION TO TREAT LESIONS CAUSED BY HERPES SIMPLEX VIRUS

(75) Inventor: Karry Whitten, Omaha, NE (US)

(73) Assignee: G2L Touch, Inc., Omaha, NE (US)

( * ) Notice: Subject to any disclaimer, the term of this patent is extended or adjusted under 35 U.S.C. 154(b) by 207 days.

This patent is subject to a terminal disclaimer.

(21) Appl. No.: 13/116,112

(22) Filed: May 26, 2011

(65) Prior Publication Data

US 2012/0071498 A1    Mar. 22, 2012

Related U.S. Application Data

(63) Continuation-in-part of application No. 12/884,698, filed on Sep. 17, 2010, and a continuation-in-part of application No. PCT/US2010/049276, filed on Sep. 17, 2010.

(51) Int. Cl.
| | |
|---|---|
| *A61K 31/522* | (2006.01) |
| *A61K 47/34* | (2006.01) |
| *A61K 31/351* | (2006.01) |
| *A61K 9/00* | (2006.01) |
| *A61K 9/08* | (2006.01) |

(52) U.S. Cl.
CPC ............ *A61K 31/351* (2013.01); *A61K 9/08* (2013.01); *C08J 2300/206* (2013.01); *A61K 31/522* (2013.01); *A61K 47/34* (2013.01); *A61K 9/0014* (2013.01)
USPC .................................................. 514/263.38

(58) Field of Classification Search
None
See application file for complete search history.

(56) References Cited

U.S. PATENT DOCUMENTS

| 4,603,122 A | | 7/1986 | Blough ............................ 514/23 |
| 4,963,555 A | * | 10/1990 | Jones et al. ............... 514/263.38 |
| 5,552,384 A | | 9/1996 | Déziel et al. ..................... 514/17 |
| 2009/0176733 A1 | | 7/2009 | Bourgougnon et al. ......... 514/54 |
| 2009/0176743 A1 | | 7/2009 | Schaffer et al. ................. 514/81 |
| 2012/0058959 A1 | * | 3/2012 | Brown et al. .................... 514/23 |

OTHER PUBLICATIONS

Gove et al., Webster's Third New International Dictionary, 1963, p. 1798.*
Herpes Simplex Virus, Merck Manual Online Edition, [retrieved on May 29, 2012]. Retrieved from the Internet <http://www.merckmanuals.com/home/print/. Revision Nov. 2009>.*
Hamuy et al., European J. Dermatology, published in 1998, retrieved on May 29, 2012, from the Internet: <http://www.jle.com/en/print/e-docs/00/01/89/10/article.phtml>, 10 pages.*
Walker et al., Advanced Drug Delivery Rev., 1996, 18, 295-301.*
Dey et al., "Enhanced Percutaneous Permeability of Acyclovir by DMSO from Topical Gel formulation" International Journal of Pharmaceutical Sciences and Drug Research (2009) vol. 1 No. 1 pp. 13-18.*
Bolger et al., "Cutaneously applied acyclovir acts systemically in the treatment of herpetic infection in the hairless mouse" Antiviral Research (1997) vol. 35 pp. 157-165.*
Nathalie H-N., et al., "Evaluation of the in vitro skin permeation of antiviral drugs from penciclovir 1%creamand acyclovir 5% cream used to treat herpes simplex infection", BMC Dermatology, vol. 9, No. 3, pp. 1-10 (Apr. 2, 2009).
Teresa H. Bacon, et al., "Herpes simplex virus resistance to acyclovir and pencyclovir after two decades of antiviral therapy", Clinical Microbiology Reviews, vol. 16, No. 1, pp. 114-128 (2003).
International Search Report and Written Opinion dated Jun. 17, 2011, Application No. PCT/US2010/049276.

* cited by examiner

*Primary Examiner* — Eric Olson
(74) *Attorney, Agent, or Firm* — Richard H. Pagliery; TechLaw LLP

(57) ABSTRACT

The present invention is generally directed toward therapeutic compositions for treating infections caused by Herpes Simplex Virus ("HSV"). The therapeutic compositions meet a long felt need in the art of providing a treatment for lesions that result from HSV that drastically reduce the duration of a cold sore when vesicles have already appeared and a treatment that will prevent the outbreak of a lesion and formation of vesicles when applied in the prodromal stage. The therapeutic compound comprises a mixture of Acyclovir ("ACV"), Penciclovir ("PCV"), and dimethyl sulfoxide ("DMSO"). The therapeutic compositions of the present invention include multiple formulations of the three active ingredients and may also include inactive ingredients and/or additional active ingredients.

18 Claims, No Drawings

THERAPEUTIC COMPOSITION TO TREAT LESIONS CAUSED BY HERPES SIMPLEX VIRUS

CROSS-REFERENCE TO RELATED APPLICATIONS

This application is a continuation-in-part application of U.S. application Ser. Nos. 12/884,698 and PCT/US2010/049276 both filed on Sep. 17, 2010, and claims priority to U.S. Application Ser. No. 61/243,251 filed on Sep. 17, 2009, all titled THERAPEUTIC COMPOSITION TO TREAT LESSIONS CAUSED BY HERPES SIMPLEX VIRUS which are incorporated by reference herein in their entireties.

BACKGROUND OF THE INVENTION

Herpes Simplex Virus ("HSV") is a family of viruses that infects a large portion of the human population. HSV occurs in at least two well known varieties, particularly Herpes Simplex Virus 1 ("HSV-1") and Herpes Simplex Virus 2 ("HSV-2"). It has been estimated that by the age of fifty (50), eighty to ninety (80-90) percent of human beings carry HSV-1 antibodies. It is also estimated that twenty to thirty (20-30) percent of the human population is infected with the HSV-2 virus. Once a person is infected, HSV remains in an inactive state in the body and may cause recurring lesions throughout the life of an infected person. The high prevalence of the human population that carries either HSV-1 or HSV-2 leads to an ever increasing number of persons who experience lesions caused by either HSV virus strain. The viruses often cause lesions on the area surrounding the mouth and/or the genital area of those carrying HSV-1 or HSV-2.

A well known example of a HSV caused lesion is a cold sore or fever blister on or around the mouth of a person infected with HSV-1 or HSV-2. A cold sore is a lesion consisting of small blisters on the lip or surrounding mouth that lasts from 5 to 14 days. These lesions are caused when vesicles form, break open, and leak a clear fluid. The lesions usually scab over after a few days and heal themselves. While these lesions usually heal themselves in 5 to 14 days, they are unsightly and may be very painful to those experiencing them. Herpes Simplex Virus lesions, other than cold sores, are similar in appearance and duration.

Most over-the-counter topical treatments for cold sores are topical anesthetics to decrease pain, skin protectants (petroleum or zinc oxide), antiseptics, or herbal remedies. Most of these topical treatments attempt to reduce the pain, discomfort and appearance of the cold sore but usually have little effect on the duration of the lesion. In addition, antiviral medications have been developed in an attempt to reduce the occurrence of lesion outbreaks and attempt to subvert the viral activity in the body. Many of these antiviral medications are administered orally. Antiviral medications have also been developed as topical treatments in an attempt to slow down the activity of the virus within the lesion and are usually most effective if administered prior to the formation of the vesicles. Two well known and commercially available antiviral compounds are Penciclovir and Acyclovir.

Penciclovir is generally poorly adsorbed orally; therefore, it is often used more as a topical treatment. Penciclovir is often available by prescription in the pharmaceutical cream DENAVIR® which contains one percent (1%) Penciclovir. Use of 1% Penciclovir cream has been found to reduce the duration of a cold sore by an average of one-half day (an average of 4.5 days treated versus 5.0 days for untreated cold sores). Acyclovir is an antiviral that is administered through oral tablets, topical cream, intravenous injection and ophthalmic cream. A five percent (5%) Acyclovir topical cream is commercially available in the topical medication ZOVIRAX™ cold sore cream. Similar to Penciclovir, 5% Acyclovir cream has also been clinically shown to reduce the duration of a cold sore by an average of one-half day.

There have been other efforts made to improve the performance of these drugs when used to combat herpes viral infections. For example, U.S. Pat. No. 6,469,015 issued to Griffiths, et al., discloses the inclusion of solubilized Penciclovir in a topical formulation comprising propylene glycol. This formulation was developed to increase the absorbance of the drug at the skin and thereby provide an increased effective dosage to the lesion area.

Synergistic combinations of antivirals with other compounds have been reported. For example, U.S. Pat. No. 5,552,384 issued to Deziel, et al., discloses the use of an antiviral nucleoside analog with a ribonucleotide reductase inhibiting peptide derivative. Such a combination was reported to have increased antiviral activity without increased toxicity.

The synergistic effects of combinations of multiple antivirals have also been reported, but without suggesting the compounds disclosed herein. For example, Sutton, et al., "Activity of Penciclovir in Combination with Azido-Thymidine, Ganciclovir, Acyclovir, Foscarnet and Human Interferons against Herpes-Simplex Virus-Replication in Cell-Culture," *Antiviral Chemistry and Chemotherapy*, vol. 4, no. 2 pg. 85-94 (1992), discloses the use of Penciclovir with other antivirals including acyclovir. However, the in-vitro studies conducted showed that the combinations of antivirals had effects that were, "purely additive."

Considering cold sores usually have a duration of 5-14 days, a one-half day reduction in the duration of a cold sore resulting from treatment with antiviral compounds known in the prior art provides little improvement over not implementing any treatment at all. As such, there is a long-felt need in the art to provide a therapeutic compound to reduce the duration and scope of lesions resulting from the Herpes Simplex Virus. One embodiment being, a treatment that will drastically reduce the duration of a cold sore when vesicles have already appeared and a treatment that will prevent the formation of vesicles and a lesion when applied in the prodromal stage.

SUMMARY OF THE INVENTION

The present invention is generally directed toward therapeutic compositions for treating lesions caused by Herpes Simplex Virus ("HSV"). The composition of the present invention meets a long felt need in the art of providing a treatment for lesions that result from HSV that drastically reduces the duration of a cold sore when vesicles have already appeared and a treatment that will prevent the formation of vesicles and a lesion when applied in the prodromal stage. The present invention is a mixture of at least two active ingredients that result in prevention of the appearance of a cold sore when applied in the prodromal stage and also drastically reduces the duration of a lesion resulting from HSV-1 or HSV-2 after the vesicles or a lesion has appeared. The therapeutic composition of the present invention comprises a mixture of Acyclovir ("ACV"), Penciclovir ("PCV"), and dimethyl sulfoxide ("DMSO"). The therapeutic compositions of the present invention include various concentrations of the at least three ingredients. Further, the composition of the present invention may include inactive ingredients.

One non-limiting embodiment of the present invention is a composition including about 3.75% of ACV, about 0.75% PCV, and about 10% DMSO by weight. Other and further embodiments and objects of the invention, together with the features of novelty appurtenant thereto, will appear in the course of the following description.

DETAILED DESCRIPTION OF THE INVENTION

There is provided herein a therapeutic composition that prevents the formation of a lesion resulting from Herpes Simplex Virus ("HSV") when administered in the prodromal stage and greatly reduces the duration of a lesion resulting from infection with HSV when administered after the lesion has appeared. The therapeutic composition of the present invention generally includes a mixture of three antiviral compounds known in the art to topically treat lesions caused by HSV. Further, the present invention may contain inactive ingredients that facilitate the administration of the composition of the present invention or make the composition of the present invention more commercially desirable.

The present invention includes a mixture of various concentrations of the following compounds: Acyclovir ("ACV"), Penciclovir ("PCV"), and dimethyl sulfoxide ("DMSO"). ACV and PCV are known antiviral compounds that may be beneficial in treating lesions caused by HSV. Both PCV and ACV are commercially available for the treatment of HSV-1 and HSV-2 infections and can be administered through a variety of known methods which may include, but are not limited to oral tablets, topical cream, intravenous injection and ophthalmic cream. DMSO is a membrane penetrant that may be particularly beneficial when used in conjunction with ACV and PCV. The composition of the present invention may also contain inactive ingredients to facilitate administration or make the composition more commercially desirable.

Acyclovir ("ACV") is also known by its official IUPAC name, 2-amino-942-hydroxethoxy)methyl)-1H-purin-6 (9H)-one. ACV has a molecular formula of $C_8H_{11}N_5O_3$ and the following molecular diagram:

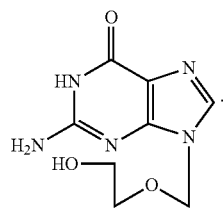

ACV is a synthetic purine nucleoside analogue that has shown both in vitro and in vivo effectiveness in inhibiting the replication of both HSV-1 and HSV-2. ACV is called a pro-drug because it is administered in an inactive or less active form and then metabolized into its active species after administration. While no mechanism of action is meant to be limiting, it is believed that the viral enzyme thymidine kinase encoded by HSV converts ACV into acyclovir monophosphate. The monophosphate is subsequently converted into diphosphate by cellular guanylate kinase and further into triphosphate by a number of cellular enzymes. Because ACV is phosphorylated into its active form only by the viral specific thymidine kinase, the active triphosphate state is confined to only the virus infected cells. Acyclovir triphosphate has been shown to stop the replication of herpes viral DNA in vitro. As a result, HSV DNA replication is stopped by the ACV derivative in three ways: (1) competitive inhibition of viral DNA polymerase, (2) the DNA chain incorporates the acyclovir triphosphate which terminates the DNA chain, and (3) the viral DNA polymerase is inactivated.

Known ACV administration methods include: oral (in tablets), topical, intravenous, and ophthalmic. ACV is thought to have poor oral bioavailability and therefore, topical or intravenous administration may be implemented to have the greatest dosage efficiency. Commonly, ACV is commercially available in 200 mg, 400 mg, 800 mg, and 1 gram tablets as well as a 5% topical cream. A five percent (5%) Acyclovir topical cream is commercially available in the topical medication ZOVIRAX™ and is used primarily for labial herpes simplex (cold sores). In this commercially available product, 5% ACV by itself has been clinically found to reduce the duration of a lesion by only 0.5 days on average.

In one embodiment of the composition of the present invention, the amount of ACV in the mixture will range from about 0.1% to 40% by weight of the total mixture. In one embodiment of the composition of the present invention, the amount of ACV in the mixture will range from about 1% to 10% by weight of the total mixture. In another embodiment of the composition of the present invention, the amount of ACV in the mixture will range from about 2% to 5% by weight of the total mixture. Further, an embodiment of the composition of the present invention will contain about 3.75% ACV by weight of the total mixture.

Penciclovir ("PCV") is also known by the official IUPAC name as 2-amino-9-[4-hydroxy-3-(hydroxymethyl)butyl]-6, 9-dihydro-3H-purin-6-one. PCV has a molecular formula of $C_{10}H_{15}N_5O_3$, and is a synthetic acyclic guanine derivative with a structure as follows:

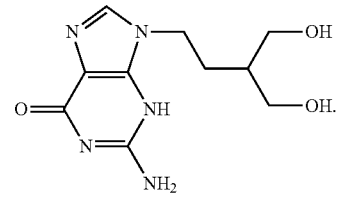 [SMILES: Nc1nc(=O)c2ncn(CCC(CO)CO)c2[nH]1]

Similar to ACV, PCV is believed to be phosphorylated by thymidine kinase to a monophosphate form, which in turn is then converted to an active state, penciclovir triphosphate, by cellular kinases. In vitro, HSV DNA synthesis and replication are inhibited by Penciclovir triphosphates inhibiting HSV polymerase competitively with deoxyguanosine triphosphate. Because PCV is phosphorylated into its active form only by the viral specific thymidine kinase, the active triphosphate state is confined to only the virus infected cells.

PCV administration may include oral (in tablets), topical, intravenous, and ophthalmic. Commonly, PCV is most widely commercially available in a 1% topical cream under the name DENAVIR®. The topical cream is available commercially by prescription and is used topically primarily for labial herpes simplex (cold sores). In this commercial embodiment, PCV by itself has been clinically found to reduce the duration of a lesion by only 0.5 days on average.

PCV and ACV are similar compounds and inhibit HSV DNA replication in much the same way. The difference between the two; however, is that the triphosphate of PCV has a very long intracellular half-life when compared to ACV's triphosphate. Therefore, it takes a lower concentration of PCV per dose than ACV to achieve the same results. This difference explains the commercial topical compounds containing 5% ACV in ZOVIRAX™ versus 1% PCV in DENAVIR®.

In one embodiment of the composition of the present invention, the amount of PCV in the mixture will range from about 0.1% to 40% by weight of the total mixture. In one embodiment of the composition of the present invention, the amount of PCV in the mixture will range from about 0.25% to 5% by weight of the total mixture. In another embodiment of the composition of the present invention, the amount of PCV in the mixture will range from about 0.5% to 1.5% by weight of the total mixture. Further, an embodiment of the composition of the present invention will contain about 0.75% PCV by weight of the total mixture.

DMSO is an aprotic polar solvent. DMSO penetrates skin and is miscible in a variety of organic solvents and water. While it is not clear, DMSO may aid in the permeation of ACV and/or PCV through the skin in an area proximate to an HSV lesion. Applicants have anecdotally observed an unexpectedly significant clinical improvement in patients with HSV lesions treated with a formulation of ACV, PCV, and DMSO.

In one embodiment of the composition of the present invention, the amount of DMSO in the mixture will range from about 1% to 40% by weight of the total mixture. In one embodiment of the composition of the present invention, the amount of DMSO in the mixture will range from about 2% to 20% by weight of the total mixture. In another embodiment of the composition of the present invention, the amount of DMSO in the mixture will range from about 5% to 15% by weight of the total mixture. Further, an embodiment of the composition of the present invention will contain about 10% DMSO by weight of the total mixture.

The composition of the present invention may also include inactive ingredients that facilitate administration of the composition of the present invention or make the present invention more commercially desirable. Such inactive ingredients may include but are not limited to: purified water, mineral oil, propylene glycol, white petrolatum, aloe, cetyl alcohol, colloidal silicon dioxide, carnauba wax, ethylhexyl palmitate, isopropyl lanolate, isopropyl myristate, medium chain triglycerides, methylparaben, octyldodecanol, alcohol, paraffin, phenyl trimethicone, polyhydroxystearic acid, propylparaben, saccharin, silica, titanium dioxide, vitamin E acetate, white wax, bee's wax, camphor, menthol, lanolin, cocoa butter, botanical extracts, saline solution, or topical anesthetics. Other ingredients may be included to increase the efficiency of topical delivery. Such ingredients may include membrane penetrants such as dimethyl sulfoxide (DMSO). In some embodiments a therapeutic compound may also include ingredients having other functionalities. For example, a variety of antiseptics may be used. While the synergistic combinations of compounds described herein are exemplary, other compounds having antiviral properties may be added. For example, lysine may be added to the composition and is known to have some anti-HSV activity.

The composition of the present invention may be administered topically, intravenously, or orally; however, the present invention is not limited to a particular method of administration. One embodiment includes a topical formulation of the composition of the present invention wherein about 3.75% ACV, about 0.75% PCV, about 10% DMSO, and the remaining about 85.5% comprising inactive ingredients of white petrolatum, propylene glycol, and mineral oil are mixed together such that the active ingredients are evenly disbursed. At the first onset of symptoms of a lesion caused by HSV-1 or HSV-2 (a cold sore), the topical formulation is applied to the infected area every 2 hours while awake.

The composition of the present invention has a synergistic additive effect that constitutes results unexpected in the art. The three compounds act synergistically to reduce the duration of the cold sore by a clinically significant amount of time.

If the composition of the present invention is applied as directed when the prodromal symptoms appear and before the vesicles of the lesions erupt, the result expected is only slight redness and no eruption of the vesicles. Therefore, the composition of the present invention may prevent the outbreak from continuing, or the viral cycle from continuing at the point of contact for immediate healing. The composition of the present invention has the potential to completely prevent an outbreak of a cold sore caused by HSV-1 or HSV-2 and substantially reduce or eliminate associated pain. This result is unexpected in the art because all known treatments for cold sores resulting from HSV-1 or HSV-2 have no known curative effects and only have been shown to slightly reduce the duration of and the pain caused by a lesion.

Even if the composition of the present invention would be applied after vesicles have appeared and erupted, the composition of the present invention is expected to greatly reduce the healing time such that, in most circumstances, the full blown cold sore would be reduced to only redness by the third day of application. When compared to the average duration of a cold sore of 4.5 days of the known compounds in the prior art (only 0.5 days less than no treatment at all), the composition of the present invention's expected healing time is an unexpected result of the combination of ACV, PCV and DMSO. Treatment with the compound is expected to significantly reduce the length of outbreaks.

In some embodiments, the mass ratio of ACV to PCV may in a range of about 1:1 to 10:1. In some exemplary embodiments, the mass ratio of ACV to PCV may be in a range of about 2:1 to 7:1. In yet other embodiments, the mass ratio of ACV to PCV may be about 5:1. In some of these various embodiments, the mass ratio of ACV to DMSO may be about 1:10 to 1:2. In some embodiments, the mass ratio of ACV to DMSO may be about 1:4.

In some embodiments, the composition may include ACV, PCV, and DMSO in the absence of any other active ingredient.

EXAMPLES

Example 1

In a first example, a patient had a lesion in the vesicle stage before any treatment had been attempted. Treatment included four applications of a compound including 3.75% ACV, about 0.75% PCV, about 10% DMSO administered over two days.

The patient of Example 1, based on the anecdotal observations to date, would be expected to report that the normal course of an outbreak, without treatment, would begin with a lesion in the vesicle stage and proceed to a lesion of such size that roughly half of the lip would be covered. The patient may also report significant pain associated with previous outbreaks was avoided with the treatment.

In anecdotal testing, post-treatment outbreaks were not observed for the duration of the follow-up period (about one year). The lack of outbreaks over such a timeframe was unusual for this patient, and it does not appear that such effective viral repression has been achieved in the past with a topical treatment.

While the examples included herein relate to the treatment of HSV-1 related lesions around the mouth, the disclosed compounds may be useful for treating other HSV-1 and HSV-2 lesions regardless of the region of the body where they occur.

From the foregoing, it will be seen that this invention is one well adapted to attain all ends and objects hereinabove set forth together with the other advantages which are obvious and which are inherent to the structure. It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

What is claimed is:

1. A therapeutic composition comprising:
Acyclovir;
Penciclovir; and
dimethyl sulfoxide.

2. The therapeutic composition of claim 1, wherein said composition comprises about 0.1 to 40% Acyclovir.

3. The therapeutic composition of claim 1, wherein said composition comprises about 0.1 to 40% Penciclovir.

4. The therapeutic composition of claim 1, wherein said composition comprises about 5 to 20% dimethyl sulfoxide.

5. The therapeutic composition of claim 1, wherein the mass ratio of Acyclovir to Penciclovir is from about 1:1 to about 10:1.

6. The therapeutic composition of claim 1, wherein the mass ratio of Acyclovir to Penciclovir is from about 2:1 to about 7:1.

7. The therapeutic composition of claim 1, wherein the mass ratio of Acyclovir to Penciclovir is about 5:1.

8. The therapeutic composition of claim 1, wherein the mass ratio of Acyclovir to dimethyl sulfoxide is from about 1:10 to about 1:2.

9. The therapeutic composition of claim 1, wherein the mass ratio of Acyclovir to dimethyl sulfoxide is about 1:4.

10. The therapeutic composition of claim 1, further comprising at least one additional antiviral ingredient.

11. The therapeutic composition of claim 1, further comprising an ingredient selected from the group consisting of mineral oil, propylene glycol, and white petrolatum.

12. A therapeutic composition comprising:
from about 2% to about 5% Acyclovir;
from about 0.5% to about 1.5% Penciclovir; and
from about 2% to about 20% dimethyl sulfoxide.

13. The therapeutic composition of claim 12, wherein said composition comprises about 2.5% Acyclovir.

14. The therapeutic composition of claim 12, wherein said composition comprises about 1% Penciclovir.

15. The therapeutic composition of claim 12, wherein said composition comprises about 10% dimethyl sulfoxide.

16. A method of treating an HSV lesion in an animal or human comprising applying the therapeutic composition of claim 1 to said lesion.

17. A method of reducing the occurrence of eruption of HSV lesions in an animal or human comprising applying the therapeutic composition of claim 1 to an HSV affected area of said animal or human.

18. The therapeutic composition of claim 12, wherein said composition comprises about 3.75% Acyclovir, about 0.75% Penciclovir and about 10% dimethyl sulfoxide.

* * * * *